US007642522B2

(12) United States Patent
Egberts (10) Patent No.: US 7,642,522 B2
(45) Date of Patent: Jan. 5, 2010

(54) DEVICE FOR IRRADIATING LIQUIDS WITH UV RADIATION IN A THROUGHFLOW

(75) Inventor: Gerhard Egberts, Bad Salzuflen (DE)

(73) Assignee: Delta UV Service Systeme, Leopoldshohe (DE)

( * ) Notice: Subject to any disclaimer, the term of this patent is extended or adjusted under 35 U.S.C. 154(b) by 233 days.

(21) Appl. No.: 11/720,297

(22) PCT Filed: Dec. 2, 2005

(86) PCT No.: PCT/EP2005/056395

§ 371 (c)(1),
(2), (4) Date: Nov. 21, 2007

(87) PCT Pub. No.: WO2006/058909

PCT Pub. Date: Jun. 8, 2006

(65) Prior Publication Data

US 2008/0210884 A1  Sep. 4, 2008

(30) Foreign Application Priority Data

Dec. 3, 2004  (DE) .................. 10 2004 058 405

(51) Int. Cl.
*G01N 21/01* (2006.01)
*G01N 21/51* (2006.01)
*G01N 23/10* (2006.01)
*G01N 23/12* (2006.01)

(52) U.S. Cl. .................. 250/429; 250/435; 250/436; 250/437; 250/504 R; 422/20; 422/24; 422/110; 422/128; 422/186.3; 422/906; 210/85; 210/105; 210/177; 210/205; 210/232

(58) Field of Classification Search .................. 250/429, 250/435–437, 504 R; 422/20, 24, 110, 128, 422/186.3, 906; 210/85, 105, 177, 205, 232
See application file for complete search history.

(56) References Cited

U.S. PATENT DOCUMENTS

| 5,124,131 A * | 6/1992 | Wekhof ................... 422/186.3 |
| 5,505,912 A * | 4/1996 | Hallett .................... 422/186.3 |
| 5,725,757 A | 3/1998 | Binot et al. |
| 2005/0269521 A1* | 12/2005 | Zagrobelny ................. 250/435 |

FOREIGN PATENT DOCUMENTS

| WO | 9109673 | 7/1991 |
| WO | 9708099 | 3/1997 |

* cited by examiner

*Primary Examiner*—Bernard E Souw
*Assistant Examiner*—Meenakshi S Sahu
(74) *Attorney, Agent, or Firm*—Marger Johnson & McCollom, P.C.

(57) ABSTRACT

The invention relates to a device for irradiating an absorbing liquid, for example waste water to be disinfected, in a throughflow. Said device comprises at least two radiator units having one cylindrical UV radiation source and three concentric sheaths. A cooling medium for carrying off heat from the UV radiation source flows in a hollow space between the inner and the center sheath. The inventive device allows to use high-performance UV radiation sources and to evenly irradiate the zones of irradiation and prevents floating particles from settling down on the radiator units.

18 Claims, 6 Drawing Sheets

DEVICE FOR IRRADIATING LIQUIDS WITH UV RADIATION IN A THROUGHFLOW

FIELD OF THE INVENTION

The invention relates to a device for irradiating absorbing liquids, for example wastewater that is to be disinfected, with UV radiation.

PRIOR ART

Devices for treating sewage treatment plant effluent for the purpose of reducing the germ count have long been known. The underlying research was published in 1984 by Scheible et al. in the publications of the Environmental Protection Agency with the title "Ultraviolet Disinfection of Waste Waters from Secondary Effluent and Combined Sewer Overflows". Various concepts of disinfection of sewage treatment plant effluent using UV radiation were investigated in detail both theoretically and practically in the course of this research, and conclusions were drawn from it. Furthermore, requirements were formulated for the design and operation of a UV installation for wastewater disinfection. The following special characteristics of the medium (wastewater) were taken into account:
- high microbiological loading of the medium
- poor UV transmittance of the medium
- tendency of the medium to form sediments
- high content of suspended matter in the medium
- high throughputs of up to several 1000 $m^3$ per hour.

A UV irradiation installation for wastewater disinfection is in principle an irradiation zone installed in the discharge point of the sewage treatment plant, through which the water flows freely or is forced to flow continuously, and the water flowing through is irradiated with UV radiation of a particular wavelength by means of suitable electrically operated sources of UV radiation. Therefore it is necessary that each volume element of the water receives a sufficient radiation dose. The radiation dose is defined as the radiation energy with microbiocidal action that is applied per unit area. The characteristics of the wastewater stated above can be converted to the following requirements for the design of UV irradiation installations:
- uniform illumination of the irradiation zone
- avoidance of large layer thicknesses of the irradiated water
- uniform flow through the irradiation zone
- as few hydraulic dead zones as possible in the irradiation zone
- adjustment of the height of the water level with fluctuating throughputs
- as few internals as possible in the water, which favour deposits of suspended matter
- easy access for cleaning and lamp changing.

Since the throughputs are as a rule high, irradiation units in the free surface flow, i.e. in the open channel, are considered almost exclusively for the UV irradiation of biologically purified wastewater. An open discharge channel, as a rule provided by the builder, is equipped with an irradiation installation that forms an arrangement of as a rule cylindrically shaped UV light sources uniformly covering the flow cross-section of this discharge channel. Depending on the arrangement of the cylindrical UV radiation sources, a distinction is made between:
- installations with a vertical arrangement of UV radiation sources. Here the cylindrical UV sources stand in quartz tubes closed on one side, in the manner of a bar screen with vertical teeth in the channel. This design has the advantage that lamp changing is possible from above, i.e. without undoing water-tight seals. A disadvantage is the unavoidable formation of rings and deposits in the zone where the water level fluctuates, which are difficult to remove.
- installations with UV radiation sources arranged horizontally in the direction of flow. Here the quartz tubes with the UV radiation sources inside are completely immersed and water flows round them in parallel. This thereby avoids the disadvantages of the lateral arrangement, however the water-tight seals have to be undone for lamp changing.

Installations with UV radiation sources arranged horizontally in the direction of flow are largely employed in current practice.

Following the aforementioned study by the Environmental Protection Agency, this technology was first launched on the market in the USA and Canada. Numerous such installations have since been installed throughout the world.

In installations according to the prior art, an open rectangular discharge channel at the discharge point of the sewage treatment plant, provided by the builder, is equipped with a set of low-pressure mercury radiators (LP-Hg radiators). Therefore each radiator is provided with a cylindrical quartz jacket tube, around which the water to be treated flows. In each case a row of jacket tubes with LP-Hg radiators arranged above one another are assembled to form a module, comprising a stainless steel frame for holding the jacket tubes arranged above one another, a top cover to prevent emission of harmful UV radiation, a plug-and-socket connector for power supply and handles for removal in the vertical direction for maintenance purposes.

For complete illumination of the channel cross-section, several such modules are secured parallel to one another in a frame that is mounted rigidly on the channel, and functions as support, fixing device and cable conduit.

LP-Hg radiators are mercury gas discharge lamps with UV-transparent lamp tubes, which emit the greater part of their radiation in the microbiocidal triplet resonance of mercury at 253.7 nm. This type of lamp typically has an electric power of less than 100 W, even in special designs (amalgam lamp). For larger installations with a throughput of 10,000 $m^3$ per hour or more, an electrical energy consumption of 20 to 30 Wh per cubic metre of water can be taken as a guide value, depending on the properties of the water. At 100 W power of an LP-Hg radiator, such an installation requires 2000 to 3000 radiators. This is already possible according to the prior art by parallel or series connection of radiator assemblies, but there are the following disadvantages:
- no economies of scale for plant costs
- large space required
- high cost of operation and maintenance
- high lamp costs.

For these reasons, UV treatment of larger effluent streams is very expensive according to the prior art. The logical step for lowering the cost is to increase the power per radiator, which immediately leads to reduction of the number of radiators and therefore the capital costs.

With LP-Hg radiators with amalgam, power ratings up to a maximum of about 300 W can be achieved. For a further increase in power, medium-pressure mercury radiators (MP-Hg radiators) are known, and depending on their design they can have an electric power rating of 10 kW or more per radiator. They emit a quasi-continuum of UV radiation at high power density, and with reference to microbiocidal UV radiation, the generating efficiency is from approx. 12% to 15%.

Previous attempts to use these high-power MP-Hg radiators for wastewater disinfection were unsuccessful, for the following reasons:

non-uniform distribution of irradiation intensity owing to the high radiation power of the individual radiators increased deposits from the wastewater and burning of these deposits onto the jacket tubes of the radiators. The reason for this is the far higher wastewater-jacket tube temperature gradient for conducting away the higher thermal power of the MP-Hg radiator.

risks of accidents and short-circuits through manipulation of the high-voltage connectors of the MP-Hg radiators in the water-soaked zone.

There is therefore a need for cost-effective installations for UV treatment of larger wastewater streams.

SUMMARY OF THE INVENTION

The invention is based on the problem of proposing an installation for flow-through UV irradiation of absorbing liquids, which permits uniform irradiation of the liquid even at high throughputs.

Another problem of the invention is to propose such a device that can be manufactured cost-effectively.

Yet another problem of the invention is to propose a device for flow-through UV irradiation of absorbing liquids, for which the maintenance costs are reduced.

The problem is solved with a device for flow-through UV irradiation of absorbing liquids, for example wastewater that is to be disinfected, by at least two assemblies of UV radiators, characterized in that one radiator assembly has a cylindrical UV light source and three concentric, cylindrical jacket tubes, with a coolant for carrying away heat from the UV radiation source flowing in a hollow space between an inner and a central jacket tube.

The coolant is able to lower the temperature on the outer jacket tube, so that burning of deposits onto the jacket tube can be prevented. It is possible to increase the diameter of the outermost jacket tube, so that it becomes possible to achieve a more uniform distribution of the irradiation intensity. The diameter of the outer jacket tube is then preferably between 80 and 250 mm, and especially between 120 and 200 mm.

The hollow space between the outer and the central jacket tube can be filled with UV-transparent gas.

The power density of the UV radiation sources, for example MP-Hg radiators, is preferably at least 10 W UV-C radiation per cm in the axial direction.

The UV radiation sources can therefore be arranged horizontally, transversely to the direction of flow, for example on a U-shaped steel shrouding, with the ends of the jacket tubes preferably sealed and mounted and provided with connections for power and coolant. To simplify maintenance, lateral service pits can be provided, giving access to the UV radiation sources and allowing them to be replaced.

To prevent emission of harmful UV radiation upwards, covers are preferably provided above the radiator assemblies.

The radiator assemblies can be arranged in longitudinal section in the pattern of two-dimensional close packing of spheres, in order to ensure the most uniform possible distribution of irradiation intensity.

For the coolant, a coolant circulating pump and a heat exchanger for releasing heat to the absorbing liquid can be provided.

Distilled water, which has very low UV absorption, can preferably be used as coolant. It is possible to add alcohol, such as ethanol or methanol, in order to prevent biological contamination of the coolant.

The jacket tubes preferably comprise UV-permeable material, for example quartz glass.

It is possible to provide throughput-dependent power control of the sources of UV radiation, so that despite variable throughput, the radiation intensity is always correct.

BRIEF DESCRIPTION OF THE DRAWINGS

Further features and advantages of the invention will become clear from the following description of a preferred example of application, referring to the appended drawings.

DETAILED DESCRIPTION OF THE INVENTION

The invention will be described in detail in the following, on the basis of a preferred embodiment.

Figure 1:
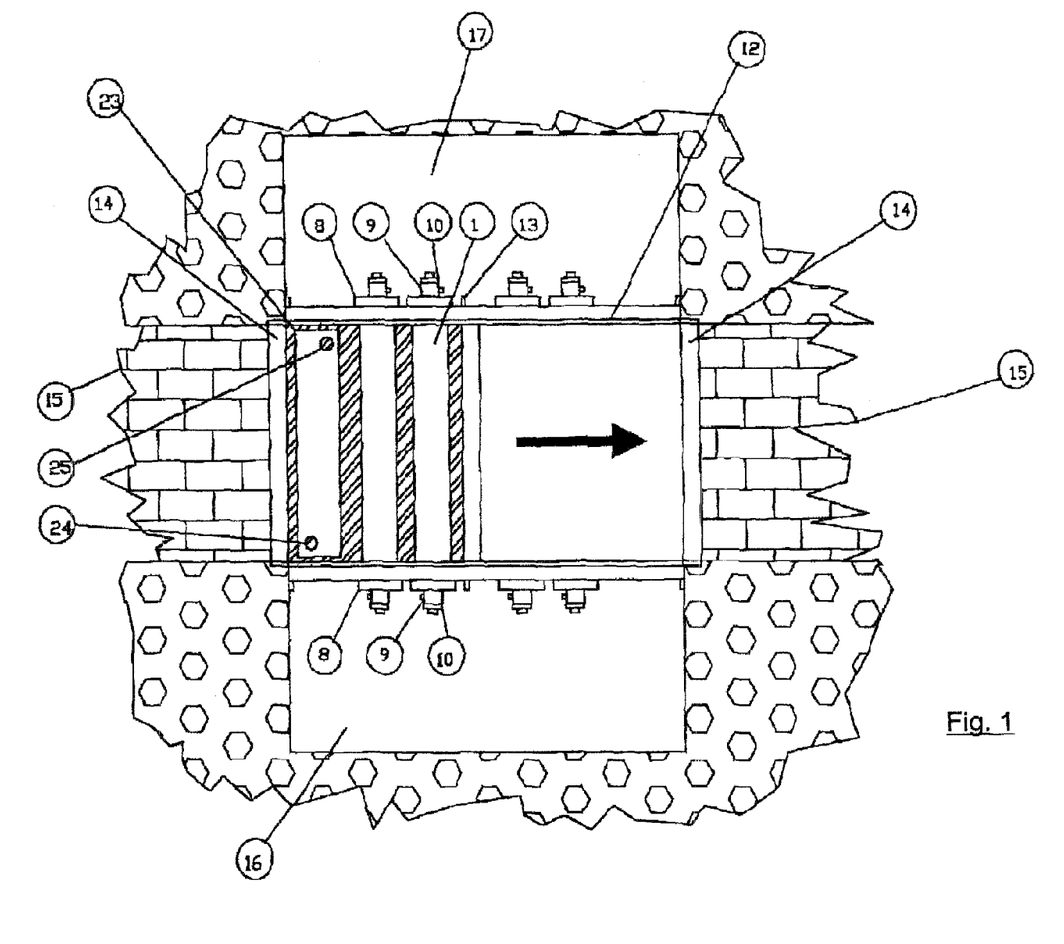
FIG. 1 shows a top view of an example of application of a device according to the invention for the flow-through UV radiation of absorbing liquids.
Figure 2:
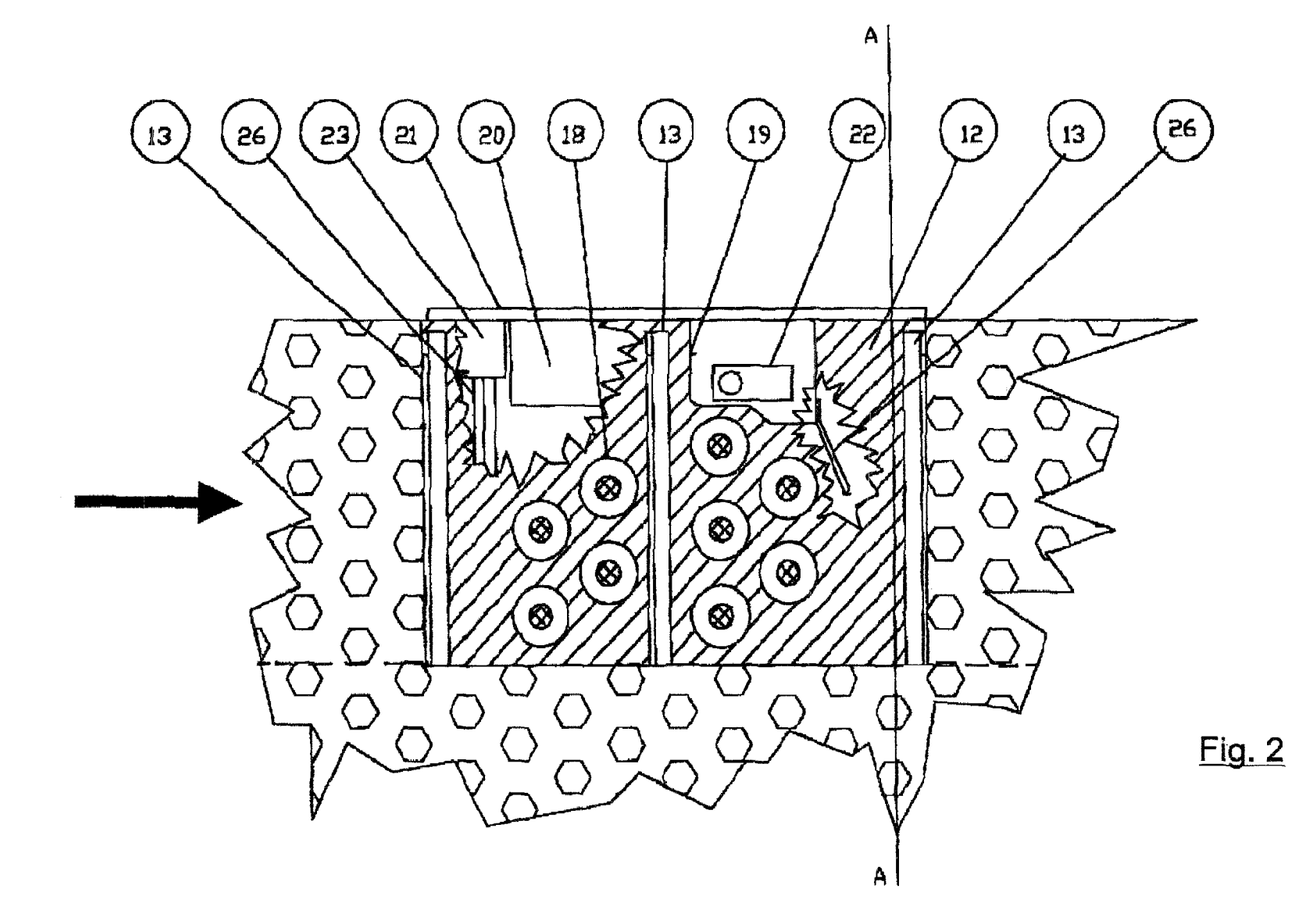
FIG. 2 shows a view in longitudinal section of the example of application in FIG. 1.
Figure 3:
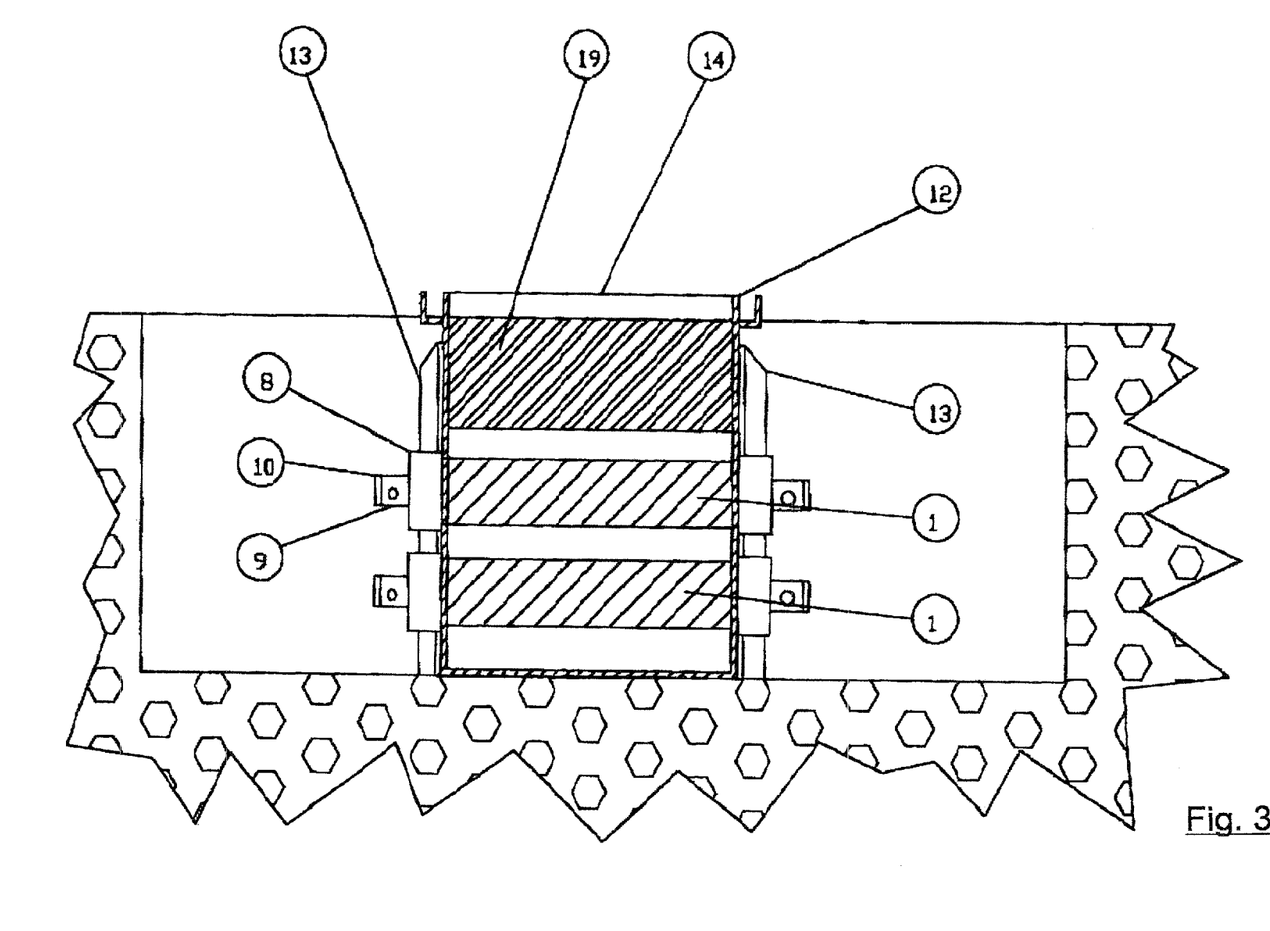
FIG. 3 shows a cross-sectional view along line A-A in FIG. 2.

The device according to the invention is shown in top view in FIG. 1, in longitudinal section view in FIG. 2 and in cross-sectional view against the direction of flow in FIG. 3. The direction of flow of the absorbing liquid is indicated with an arrow, but is of no importance for the functionality of the device according to the invention. A U-shaped stainless steel wall 12, which is kept dimensionally stable by external stiffeners 13 and diagonal members 14 arranged above the surface of the liquid, is installed in channel 15. On each side there is a covered pit 16, 17, through which all electrical connections, control lines and pipes or hoses of the coolant circuit are led, and are accessible for maintenance purposes. In the two lateral vertical zones of the stainless steel wall 12 there are circular openings 18 in pairs opposite one another, into which the radiator assemblies, namely outer jacket tube 1, holders and covers 8, 9 and 10 are inserted and made water-tight. The electrical connecting cables and coolant hoses are not shown. Most preferably, they are led through a cable conduit, also not shown, on the vertical stiffener 13. The irradiation zone is covered at the top via one or more stainless steel caissons 19, 20, which ensure that even at high water throughput above the uppermost radiator assembly the maximum distance from the radiator assembly predetermined by the irradiation geometry (i.e. the clearance between caisson and upper radiator assembly) is not exceeded. Conversely, a weir in the flow direction after the irradiation zone ensures instead that the bottom edge of the caisson always remains wetted and in particular the uppermost radiator assembly does not in any circumstances dry out completely or partially. The caisson can either be welded into the stainless steel wall solidly as a stabilizing cover, or it can be of detachable design to allow better accessibility to the irradiation zone for cleaning purposes. Above it, there is a walk-on cover 21, which can also serve as base plate for a switch cabinet with the power supply and the necessary control and monitoring equipment, if this is to be positioned directly on the installation. The solidly welded-in caisson 19 serves for mounting a coolant circulating pump 22 and as cable shaft, if the switch cabinet is mounted on the cover.

In the flow direction, before the irradiation zone there is a heat exchanger 23, via which the heat energy of the MP-Hg radiators absorbed by the coolant is released to the liquid stream. It consists of a distribution chamber with connector for the feed line 24, plenum chamber with connector for the outlet line 25 and, between them, U-shaped copper tubes 26, which dip into the water from above and transfer the waste heat to the wastewater stream that is to be treated.

The heat exchanger serves at the same time as a screen against UV radiation emitted forwards from the irradiation zone and as an obstacle to flow for evening out the flow through the irradiation zone.

In the direction of flow, after the irradiation zone there is finally a baffle plate 26 pointing obliquely downwards, which on the one hand optimizes flow guidance at the top edge of the irradiation zone and on the other hand serves as a screen against UV radiation emitted backwards from the radiation zone.

Figure 4:
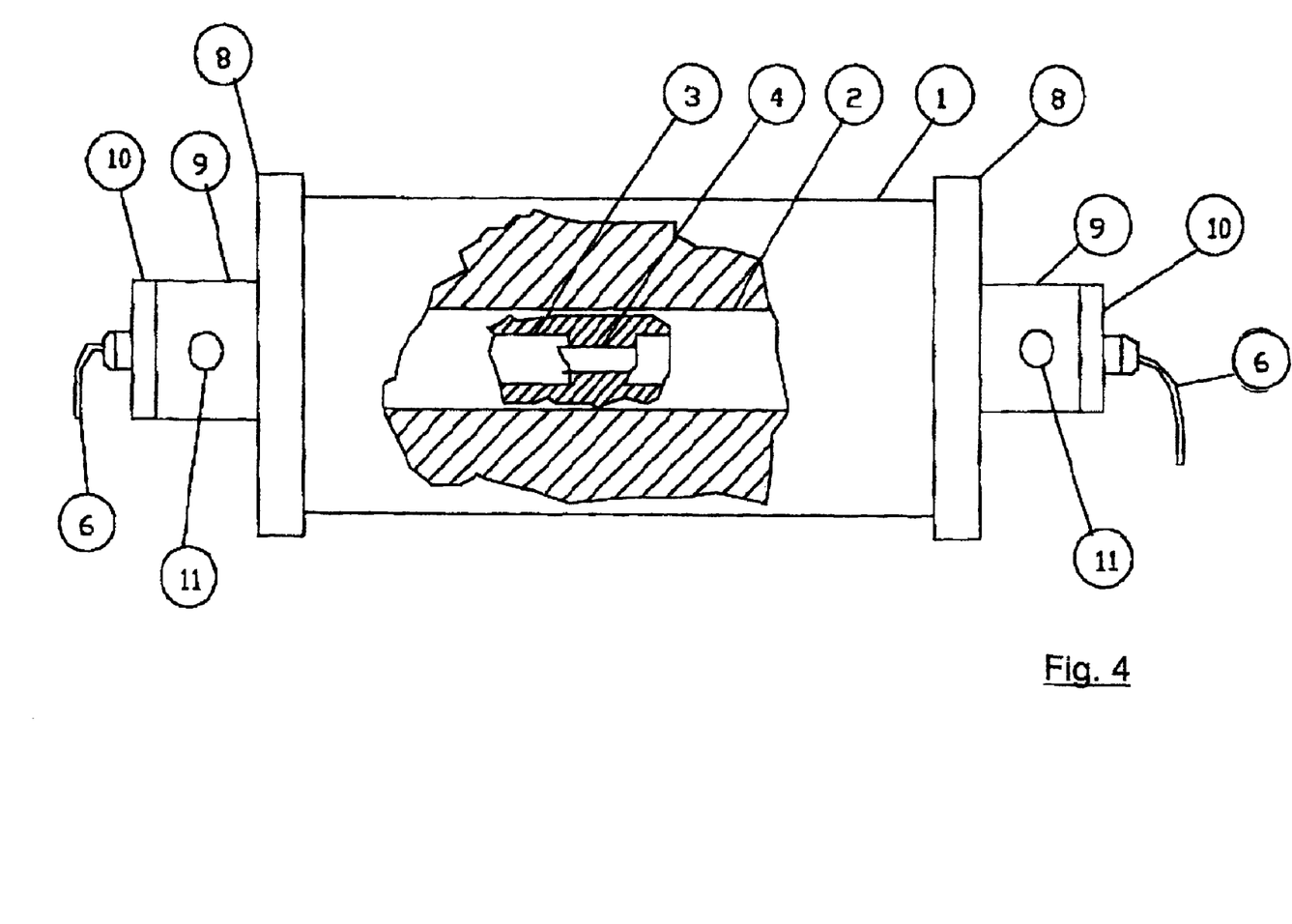
FIG. 4 shows an example of application of a radiator assembly according to the invention.
Figure 5:
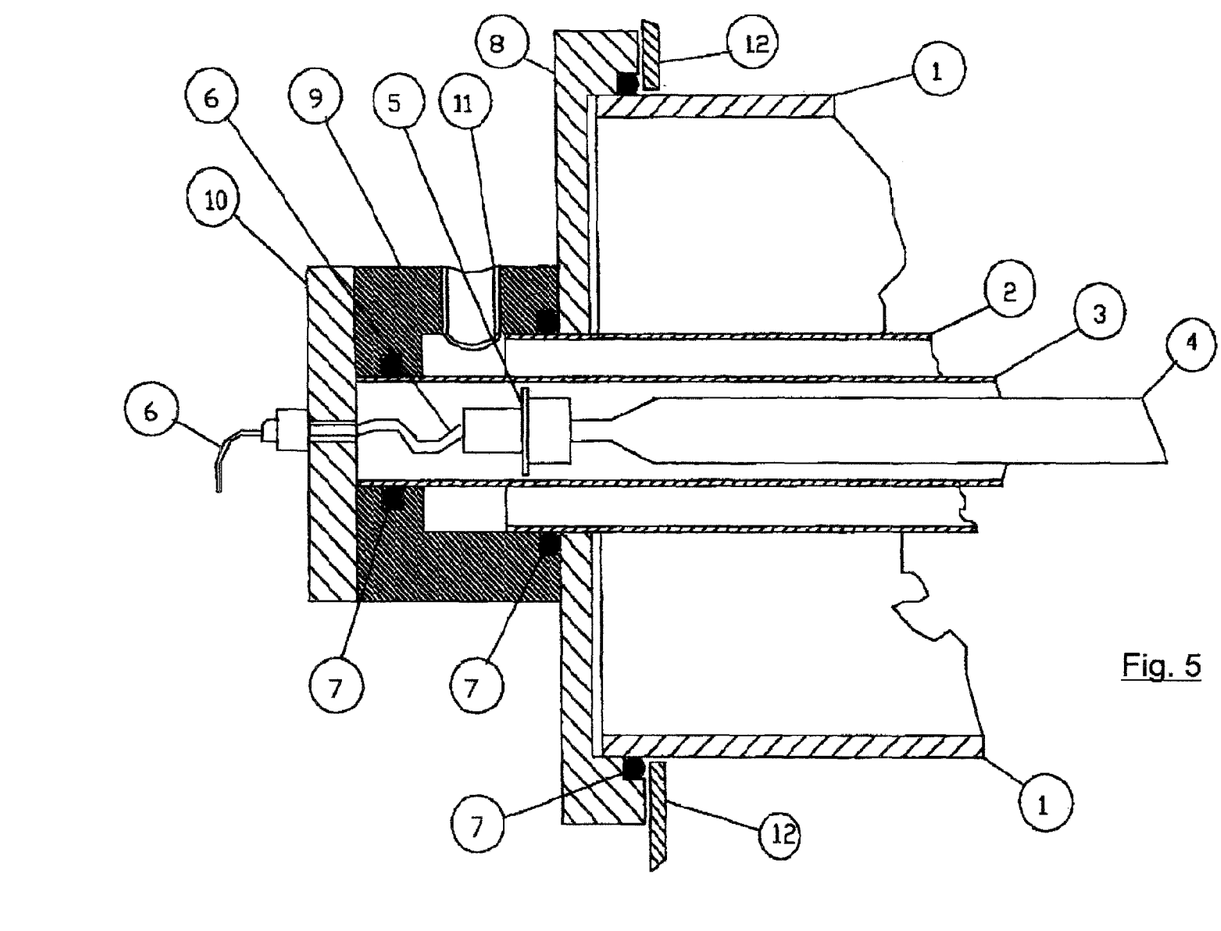
FIG. 5 shows a detail view of the radiator assembly in FIG. 4.

The radiator assembly will be explained in detail below, referring to FIGS. 4 and 5. It consists of a centrally arranged, cylindrical UV radiator, for example an MP-Hg radiator with a power rating of at least 10 W UV-C radiation per centimetre in the axial direction, which radiation source 4 is provided with a holder 5 and electrical connectors 6. An outer jacket tube 1, middle jacket tube 2 and inner jacket tube 3, preferably made of UV-permeable quartz glass, are arranged concentrically to the UV radiation source 4 and are sealed with lateral holders 8, 9 having O-ring seals 7, plus an end cover 10. In addition, connectors 11 are provided for circulation of the coolant in the hollow space between the inner jacket tube 3 and the middle jacket tube 2.

The more uniform distribution of the irradiation intensity on the absorbing liquid that is possible according to the invention will be illustrated in the following as an example with a water throughput of 10,000 m$^3$/h, equivalent to 2777 l/s.

Let us assume the use of 50 MP-Hg radiators per 10 kW of electric power, a generating efficiency of the UV radiation of 15%, and length of the light source of 100 cm, an outside diameter of the (outer) jacket tube of 4 cm according to the prior art and a UV permeability of the wastewater of 80%/cm.

Then an irradiation intensity of approx. 1.2 W/cm$^2$ is calculated for the outside surface of the jacket tube, an irradiation intensity of approx. 0.65 W/cm$^2$ at a distance of 1 cm and an irradiation intensity of approx. 0.38 W/cm$^2$, corresponding to less than a third, at a distance of 2 cm.

If we consider the space in which the irradiation intensity drops from 100% to approx. 33%, this is approx. 3.8 l per jacket tube. With 50 radiators we get a total space of 190 l. The 2777 l/s water throughput according to this example cannot be led through such a small irradiation zone. The very high surface load with thermal energy that is to be led away leads moreover to strengthened formation and burning-on of deposits on the outer jacket tube, which in its turn leads to increasing absorption of radiation in the layer of contaminants.

With an outside diameter of the outer jacket tube 1 of 10 cm (20 cm) the irradiation density in the above example on the jacket tube is 0.477 (0.238) W/cm$^2$ and at a radial distance of 3 cm (3.5 cm) it drops back to about a third, namely 0.153 W/cm$^2$ (0.08 W/cm$^2$). The associated volume per UV source is approx. 12.2 l (26 l), corresponding to 1300 l total volume for 50 radiators. Enlargement of the outer jacket tube thus permits far higher throughputs of the liquid that is to be irradiated. However, this requires effective removal, by the coolant, of the heat produced by the high-power UV radiation source. Conversely, the coolant must absorb as little UV radiation as possible itself, so that the coolant flows through a relatively "thin" hollow space between the inner jacket tube 3 and the middle jacket tube 2, preferably with distilled water as coolant on account of the low UV absorption, if necessary with addition of ethanol to prevent the development of bacteria and algae. Owing to the low UV absorption, the jacket tubes 1, 2, 3 are preferably made of quartz glass.

Figure 6:
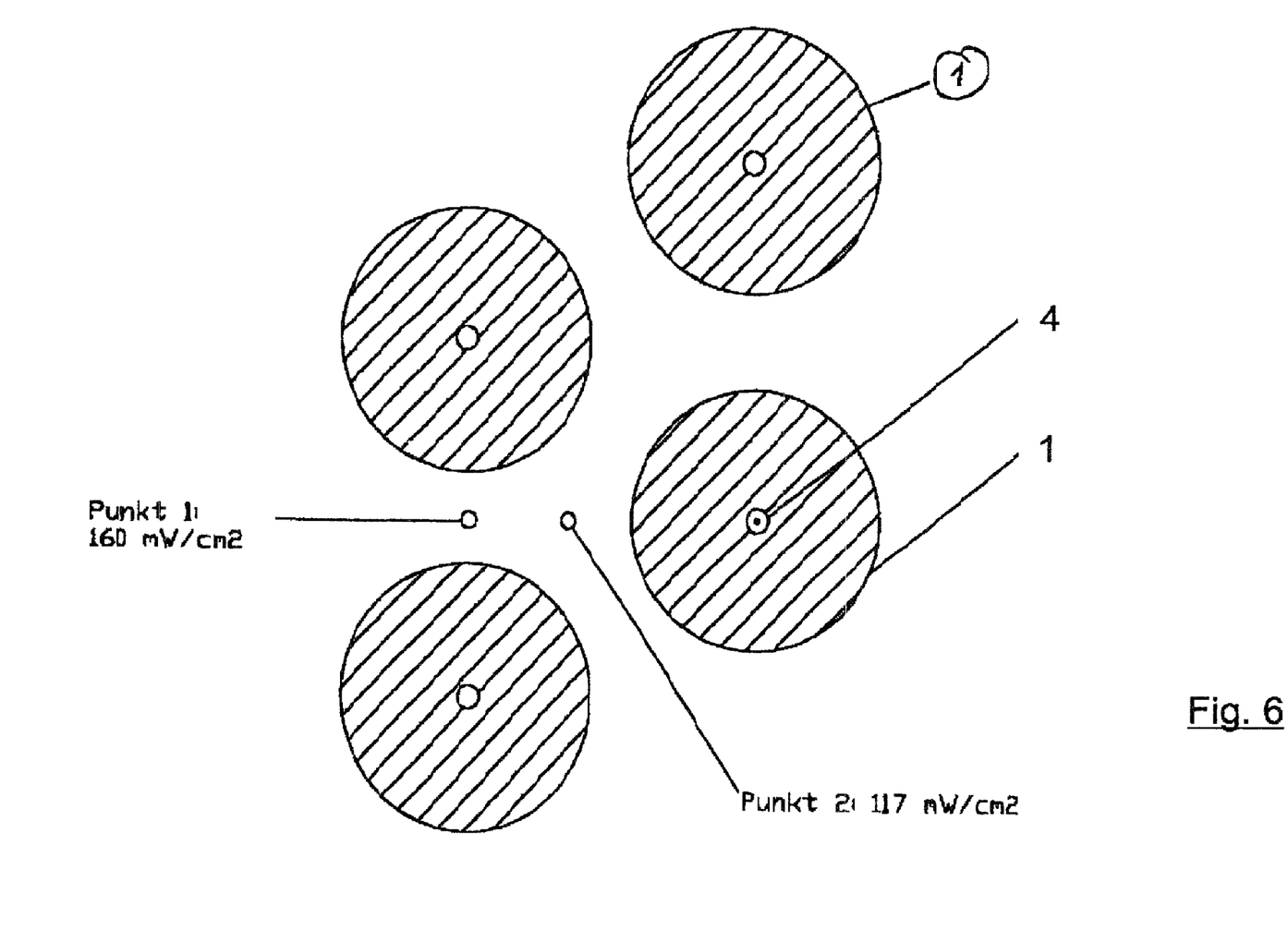
FIG. 6 shows an example of the arrangement of several radiator assemblies for achieving uniform irradiation intensity.

Through the interaction of several radiator assemblies, the irradiation intensity can be evened out considerably, as shown schematically in FIG. 6. This shows a number of MP-Hg radiators with a diameter of the outer jacket tube 1 of 20 cm, which have a radiation power of 15 W/cm and a minimum distance of 7 cm between two adjacent radiators following the pattern of two-dimensional close packing of spheres. Based on an irradiation intensity of 0.238 W/cm$^2$ (see above) at the surface of the outer jacket tube 1, with a UV-permeability of the water of 80% per centimetre, calculation gives an irradiation intensity of max. 0.16 W/cm$^2$ by superimposing two radiators at point 1 and min. 0.117 W/cm$^2$ by superimposing three radiators at point 2.

The desirable enlargement of the outer jacket tube 1 requires additional measures for removing the heat energy associated with operation of the high-power UV source. As the removal of heat by convection with downstream transfer of heat to the medium that is to be irradiated is no longer adequate at the increased distances of several centimetres with a larger jacket tube, according to the invention a total of three quartz tubes 1, 2, 3 are provided for each radiator assembly, namely the inner jacket tube 3, the middle jacket tube 2, and the outer jacket tube 1 round which the liquid that is to be irradiated flows. This offers the possibility of circulating fully desalinated water or some other sufficiently UV-permeable liquid or gaseous coolant through the hollow space between inner jacket tube 3 and middle jacket tube 2. Owing to the absorption and the high heat capacity of the coolant, the energy of the thermal radiation will largely be carried away, in contrast to cooling by a blower, and on the whole a very uniform temperature of UV source 4 will be achieved. As a result, warming of the liquid-wetted outer jacket tube 1, which promotes deposit formation, can be avoided almost completely.

An important advantage of the device according to the invention is effective avoidance of deposits on the outer jacket tube round which the liquid that is to be irradiated flows. In conventional systems, all the heat energy produced in the UV source is transferred via the jacket tube to the liquid that is to be irradiated. This necessarily leads to a jacket tube-water temperature gradient. This can lead to deposition of particles on the outside surface of the jacket tube, especially at low flow velocities, so that absorption of the UV, VIS and IR radiation further increases this temperature gradient. The result is that formation of deposits is further accelerated. Finally, really dark, solid crusts form, which are difficult to remove.

The heat transfer at a solid-fluid phase boundary is given by:

$$Q = \alpha \cdot A (\vartheta - T), \text{ where}$$

Q is the heat flux in watts $\alpha$ is the heat transfer coefficient in watts per m$^2$ and $^\circ$ K., A is the area of heat transmission in m$^2$, $\vartheta$ is the temperature in the fluid in $^\circ$ K., and T is the wall temperature in $^\circ$ K.

For a tube around which water flows at a velocity v (in m/s), the following approximation for $\alpha$ is given in the literature:

$\alpha = (500 \text{ to } 1800) \times \sqrt{v}$, depending on surface finish.

The problem of effectively keeping the outer jacket tube clean can be formulated as follows: for a given power rating, the temperature difference ($\vartheta$–T) given in the above equation must be kept small enough, under all operating conditions, so that the self-intensifying fouling process described above can be avoided. Investigations have shown that with the arrangement according to the invention, avoidance of fouling can largely be achieved if the thermal power that is to be carried away at an average flow velocity of 2 m/s can be kept below approx. 2000 W/m², corresponding to a temperature difference ($\vartheta$–T) of 1 to 3 kelvin for the range of $\alpha$ given above.

Factors contributing to keeping the surface largely clear of deposits are, on the one hand, the restriction of the temperature of the outer jacket tube resulting from the interaction of the reduced thermal power per unit area and heat abstraction through the increased tangential velocity, and on the other hand the fact that the surface is kept clean by the abrasive forces of the water flowing past.

At low flow velocities, if the lamp power is also reduced, the deposits only form a thin film on the surface of the jacket tube, and this is washed away again at full flow.

The requirements on thermal load per unit area and the tangential velocity can be translated into concrete geometric requirements for an example of MP-Hg radiators for wastewater disinfection on the basis of the following typical data:

| | |
|---|---|
| Discharging distance: | 100 cm |
| UV-C radiation power: | >1200 W |
| Depth of penetration in the water: | 3 cm (return to 1/e) |
| Required average dose: | 40 mJ/cm² according to formula (1) given below |
| Indication of rows of lamps one after another: | at least 2 for adequate mixing. |

Then, from the restriction of the power per unit area to less than 2000 W/m² taking into account heat abstraction via the coolant of approx. 50% of the total power, we find a minimum diameter of the outer jacket tube 1 of 8 cm. Limitation of the clearance between adjacent quartz tubes can be deduced from the required tangential velocity. The following approximate formula is used for the UV dose:

$$\text{Dose (mJ/cm}^2\text{)} = \frac{\text{UV} - \text{power (W)} \cdot \text{penetration depth (cm)}}{\text{flow (l/s)}} \quad (1)$$

On solving with respect to the flow, using a minimum velocity of the water of 2 m/s we get a maximum free cross-section of 900 cm² per radiator, corresponding to a maximum clearance between two adjacent jacket tubes of 9 cm.

The invention claimed is:

1. A device for flow-through UV irradiation of absorbing liquid having at least two UV radiator assemblies with a cylindrical UV radiation source, arranged around three concentric jacket tubes, with a coolant for carrying away the heat of the UV radiation source flowing between an inner and a middle jacket tube, where the liquid to be irradiated flows round, and the liquid to be irradiated only comes into contact with the outer of the three jacket tubes.

2. The device according to claim 1, wherein the hollow space between the outer jacket tube and the middle jacket tube is filled with gas.

3. The device according to claim 1, wherein the outside diameter of the outer jacket tube is between 80 and 250 mm, preferably between 120 and 200 mm.

4. The device according to claim 1, wherein the UV radiation source has a power density of at least 10 W UV-C radiation per cm in the axial direction.

5. The device according to claim 1, wherein the UV radiation source is a medium-pressure Hg radiator.

6. The device according to claim 1, wherein the at least two cylindrical UV radiation sources are arranged horizontally, transversely to the direction of flow of the absorbing liquid.

7. The device according to claim 6, wherein the at least two UV radiation sources are fitted on both sides of a U-shaped steel wall provided with circular openings.

8. The ee device according to claim 7, wherein both ends of the three concentric jacket tubes are mounted and sealed against the U-shaped steel wall, and on said ends there are connectors for electric power and for the coolant.

9. The device according to claim 1, having covers that prevent emission of UV radiation upwards.

10. The device according to claim 8, having at least one service pit arranged laterally in the direction of flow of the absorbing liquid, to permit maintenance and replacement of the UV radiation sources without dismantling components that are in contact with water.

11. The device according to claim 6, wherein several UV radiation sources are arranged in the longitudinal section following the pattern of two-dimensional close packing of spheres.

12. The device according to claim 1, having a coolant circulating pump and a heat exchanger for transferring the heat energy absorbed by the coolant to the stream of the absorbing liquid.

13. The device according to claim 12, wherein the heat exchanger serves simultaneously as screening against UV radiation emitted forwards in the direction of flow and as an obstacle to flow for evening out the flow through the irradiation zone.

14. The device according to claim 1, wherein distilled water with addition of alcohol is used as coolant.

15. The device according to claim 1, having adjustment of the power of the UV radiation sources as a function of the flow rate.

16. The device according to claim 1, wherein the clearance between the outer jacket tubes of two UV radiation sources arranged one above the other is selected in such a way that the tangential velocity of the water at the surface of the outer jacket tube expressed in m/s is greater than the numerical value of the power density of the UV radiation emitted through the outer jacket tube expressed in W/cm².

17. The device according to claim 1, wherein the absorbing liquid is wastewater that is to be disinfected.

18. A sewage treatment plant, having an irradiation device for flow-through UV irradiation of absorbing liquid having at least two UV radiator assemblies with a cylindrical UV radiation source, arranged around three concentric jacket tubes, with a coolant for carrying away the heat of the UV radiation source flowing between an inner and a middle jacket tube, where the liquid to be irradiated flows round, and the liquid to be irradiated only comes into contact with the outer of the three jacket tubes.

* * * * *

UNITED STATES PATENT AND TRADEMARK OFFICE
CERTIFICATE OF CORRECTION

PATENT NO. : 7,642,522 B2  Page 1 of 1
APPLICATION NO. : 11/720297
DATED : January 5, 2010
INVENTOR(S) : Gerhard Egberts It is certified that error appears in the above-identified patent and that said Letters Patent is hereby corrected as shown below:

Column 8, line 15, the words "The ee" should read -- The --.

Signed and Sealed this

Sixteenth Day of March, 2010

David J. Kappos
*Director of the United States Patent and Trademark Office*